United States Patent [19]

Marcuse et al.

[11] 4,161,656

[45] Jul. 17, 1979

[54] METHODS FOR MEASURING DOPANT CONCENTRATIONS IN OPTICAL FIBERS AND PREFORMS

[75] Inventors: Dietrich Marcuse, Lincroft; Herman M. Presby, Highland Park, both of N.J.

[73] Assignee: Bell Telephone Laboratories, Incorporated, Murray Hill, N.J.

[21] Appl. No.: 890,869

[22] Filed: Mar. 28, 1978

[51] Int. Cl.² .......................... G01T 1/10; G01N 21/38
[52] U.S. Cl. .................................. 250/459; 250/461 R
[58] Field of Search ........... 250/302, 303, 458, 461 R, 250/459

[56] References Cited

U.S. PATENT DOCUMENTS

| 3,434,774 | 3/1969 | Miller | 350/96 WG |
| 4,025,156 | 5/1977 | Gloge et al. | 350/96 WG |

OTHER PUBLICATIONS

The Bell System Technical Journal, "Multimode Theory of Graded–Core Fibers", vol. 52, No. 9, Nov. 1973, pp. 1563–1578.

Primary Examiner—Alfred E. Smith
Assistant Examiner—Janice A. Howell
Attorney, Agent, or Firm—Sylvan Sherman

[57] ABSTRACT

Techniques are disclosed for determining the distribution of dopants in optical fibers and fiber preforms by observing the reaction of a fiber/preform to uv illumination. One technique measures the fluorescence induced by the uv. A second method measures the absorption of uv by the dopants. Thus, by determining the intensity distribution of radiant energy from the fiber/preform, the dopant distribution can be determined as a function of distance from the center of the fiber/preform.

5 Claims, 8 Drawing Figures

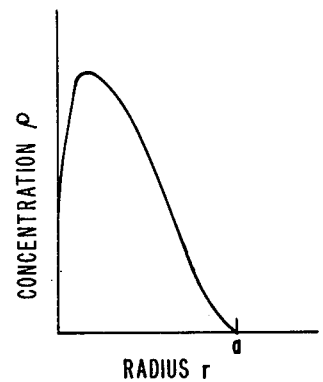
FIG. 4
FIG. 5
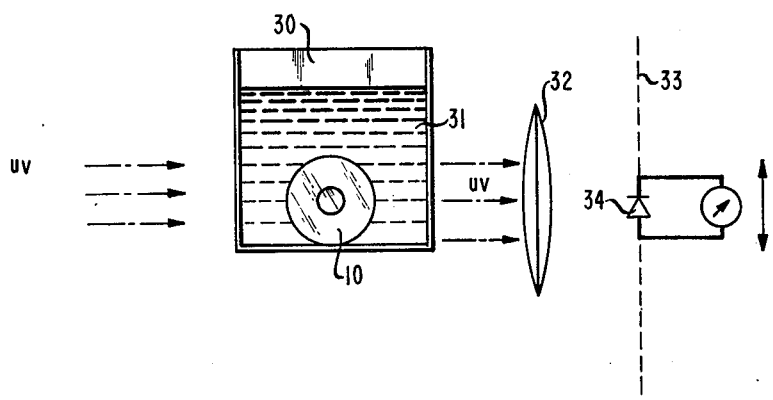
FIG. 7
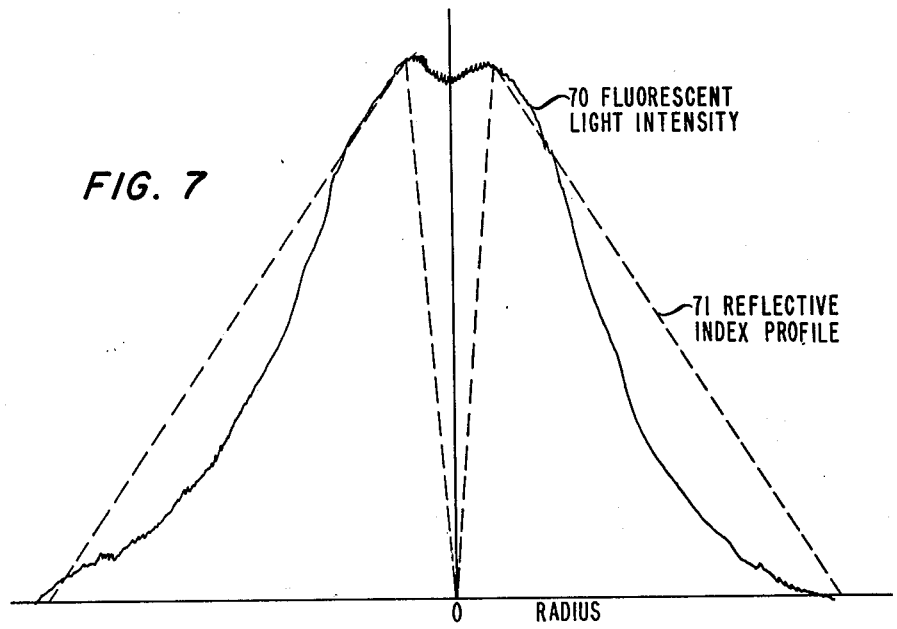

METHODS FOR MEASURING DOPANT CONCENTRATIONS IN OPTICAL FIBERS AND PREFORMS

TECHNICAL FIELD

This invention relates to methods for determining the refractive index profile of optical fibers and fiber preforms by determining the concentration and distribution of index-modifying dopants within the fibers and preforms.

BACKGROUND OF THE INVENTION

In U.S. Pat. No. 3,434,774, it is disclosed that more efficient transmission of optical wave energy along a multimode optical fiber is achieved by grading the refractive index of the fiber core. However, the degree of efficiency that can be derived is determined by how closely the fiber's refractive index profile approaches the optimum distribution. Thus, an accurate knowledge of the profile is necessary in order to assess the fiber's transmission properties.

At present, the most sensitive technique used to obtain fiber profile information is interference microscopy. In application, a very thin transverse sample of the fiber to be tested is prepared and, when placed in one branch of an interferometer, serves as a phase object. Because of its graded-index, the phase shift produced by the core region of the fiber sample is not uniform, resulting in a displacement in the fringe pattern produced by the interferometer. The fringe displacement, or shift, at any point, is proportional to the index difference, $\Delta n$, between the cladding index, which is typically uniform, and the core index at that point. Thus, to obtain the index distribution over the area of the core, the fringe displacement must be carefully measured at a large number of points consistent with the degree of accuracy desired.

The principal problem with this technique is that it is destructive in that a sample of the fiber must be taken. In addition, a very time consuming preparation of the sample is required.

In an alternative method described by D. Gloge and E. A. J. Marcatili in an article entitled "Multimode Theory of Graded-Core Fibers," published in the Bell System Technical Journal of November 1973, pp. 1563-1578, the index profile is derived from the near- and far-field power distribution. However, this technique requires a fixed length of fiber; must be corrected for leaky modes; cannot be used on preforms; and the resulting profile is only an average over the length of the sample.

SUMMARY OF THE INVENTION

Grading of the refractive index of an optical fiber is typically achieved by varying the concentration of one or more index-modifying dopants within the glassy matrix of a fiber preform. Thus, if the concentration and distribution of the dopants are known, the index profile can be determined. Thus, in accordance with the present invention, the concentration and distribution of the index-modifying dopants are determined by means of a method characterized by the steps of: illuminating a length of the fiber or fiber preform with ultraviolet radiation; determining the distribution of radiant energy derived from the fiber/preform along a direction transverse to its longitudinal axis; and determining, from the energy distribution, the concentration of dopant as a function of distance from the center of the fiber/preform.

In a first embodiment of the invention, the dopant to be measured is caused to fluoresce, and the distribution of the fluorescent light intensity is measured.

In a second embodiment of the invention, the energy distribution of the ultraviolet light that traverses the fiber/preform is measured.

It is an advantage of the invention that both fibers and preforms can be measured. It is a further advantage that the measurement is nondestructive of either fiber or preform, and no preparation of samples is required. In addition, the profile can be measured at any position along the length of a fiber or preform and is not restricted to any particular sample. It is another advantage of the method that it gives separate information about the density and distribution of each of the index-modifying dopants, thus providing valuable information about the behavior of each of the dopant materials. Such information can enable the fiber and preform manufacturer to make improvements in the fabrication process. Finally, the entire process can be automated and results obtained within a matter of minutes.

BRIEF DESCRIPTION OF THE DRAWINGS

FIG. 4 shows a typical plot of dopant concentration as a function of core radius;

FIG. 5 shows a second embodiment of the invention;

FIG. 7 shows the measured fluorescent light intensity from the preform of FIG. 6 and the refractive index profile as determined from the measured light intensity.

DETAILED DESCRIPTION

Figure 1:
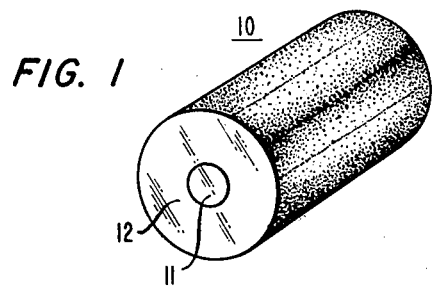
FIG. 1 shows a portion of a typical fiber/preform to which the present invention relates.

Referring to the drawings, FIG. 1 shows a portion of an optical fiber 10 comprising an inner core region 11 surrounded by a cladding 12. FIG. 1 is equally representative of a fiber preform and, insofar as the present invention is concerned, all references to an optical fiber are equally applicable to fiber preforms and, for this reason, the term "fiber/preform" is used hereinafter.

Figure 2:
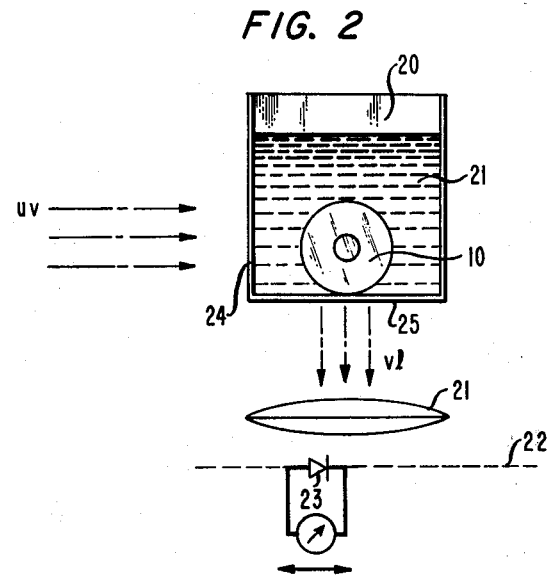
FIG. 2 shows a first embodiment of the invention.

Typically, in a multimode optical fiber, the refractive index of the core is graded, being a maximum at the center of the fiber and decreasing to some minimum value at the core-cladding interface. The grading is for the purpose of minimizing mode dispersion and, as noted hereinabove, the degree to which this is accomplished depends upon how closely the grading follows the optimum profile for the particular materials used in the fabrication of the fiber. Accordingly, it is highly desirable to be able to ascertain the concentration and distribution of index-modifying dopants in the fiber or, preferably, in the preform before the fiber is drawn. In either case, this is accomplished, in accordance with the present invention, by exposing the fiber/preform to ultraviolet radiation and measuring the distribution of radiant energy from the fiber/preform thus exposed. One way this is done is illustrated in FIG. 2 which shows a portion of a fiber/preform 10 illuminated by a source of ultraviolet radiation (uv) from a suitable source (not shown). The frequency of the uv is selected to cause the particular dopant of interest to fluoresce. The resulting visible light (vl) is focused by suitable optical means 21 onto a plane 22 which is then scanned by photooptical means 23.

Figure 3:
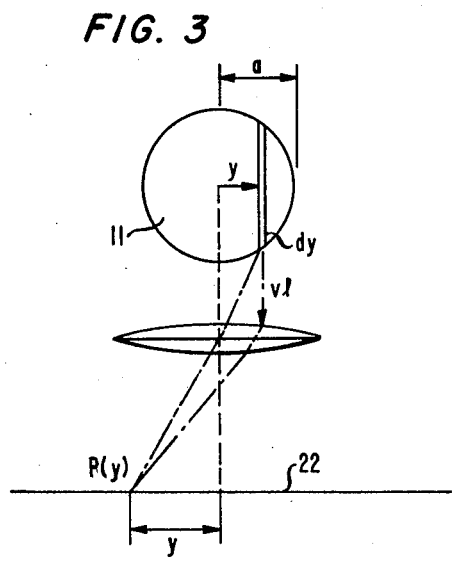
FIG. 3, included for purposes of explanation, shows the relationship between the measured light intensity and its source within the fiber/preform core.

Advantageously, fiber/preform 10 is placed within a container 20 which is filled with a material 21 whose refractive index matches that of the fiber/preform cladding, and does not fluoresce at the wavelength of interest. By making the surfaces 24 and 25 normal to the incident uv and the emergent vl, and using an index-matching material as described, the solution of the optical problem is greatly simplified. Specifically, the problem involves relating the intensity P(y) of the vl measured along the image plane to the concentration of dopant $\rho(r)$ within the core as a function of radius. The problem is illustrated in FIG. 3 which shows core 11 from which visible light is being emitted along a differential segment, dy, a distance y from the core center. The light, which is measured along the focal plane 22, is made up of light issuing from within segment dy from a dopant whose concentration varies as a function of radius. It can be shown that the relation between P(y) and $\rho(r)$ is given by $$P(y) = K \int_y^a \rho(r) \frac{r}{\sqrt{r^2 - y^2}} dr, \qquad (1)$$

where
K is a constant;
and a is the radius of the core.

More specifically, what is desired is an explicit expression for $\rho(r)$ in terms of the light intensity P(y), which is measured along the focal plane 22. By suitable transformation, this is given by $$\rho(r) = -\frac{2}{\pi K} \int_r^a \frac{dP(y)}{dy} \frac{dy}{\sqrt{y^2 - r^2}}. \qquad (2)$$

Thus, by taking measurements of the light intensity along the focal plane in a direction transverse to the fiber/preform axis, and solving equation (2), the dopant concentration as a function of radius is obtained. A curve, of the type illustrated in FIG. 4, can then be plotted and the index profile, which is proportional to the dopant concentration, determined. If more than one dopant is present, the concentration of each dopant is ascertained in the same way, and the resultant profile determined as explained in U.S. Pat. No. 4,025,156.

The process can be repeated all along the length of the fiber/preform, as required, to ascertain the uniformity of the dopant distribution along the fiber/preform.

In a second embodiment of the invention, illustrated in FIG. 5, the fiber/preform 10 is similarly exposed to ultraviolet light, as described hereinabove. However, instead of measuring the resulting fluorescence, the variation in the attentuation of the ultraviolet due to absorption within the fiber/preform is measured. Thus, in FIG. 5, optical means 32 are provided for focusing the ultraviolet that has traversed the fiber/preform, and suitable means 34 are provided for measuring the intensity of the ultraviolet along the focal plane 33. The relationship between the dopant concentration as a function of the measured intensity distribution in this case is also given by equation (2) above. As in the previous method, the fiber/preform is advantageously immersed in an index-matching fluid 31.

Figure 6:
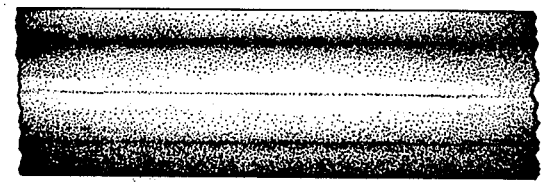
FIG. 6, included by way of example, is a drawing of a photograph of a fluorescing fiber/preform.

By way of example, FIG. 6 is a drawing of a photograph of a fluorescing fiber preform comprising a silicon dioxode rod to which germanium was added by means of the modified chemical vapor deposition (MCVD) process to produce a graded index core region. The incident ultraviolet was at a wavelength of 3560 Angstroms. This is slightly higher than the peak absorption wavelength for germanium, which is in the neighborhood of 2500 Angstroms, and is chosen so as to produce fluorescence throughout the preform. At 2500 Angstroms too much of the ultraviolet is absorbed, producing little or no fluorescence along the side of the preform away from the ultraviolet source.

Curve 70 in FIG. 7 shows the measured fluorescent light intensity and curve 71 shows the refractive index profile as determined from the measured light intensity in accordance with equation (2). In this particular preform, the index profile varies linearly. The dip in light intensity at the preform center, corresponding to the dark line in the photograph, is due to the evaporation of the index increasing dopant during the collapsing step in the fabrication of the preform. This shows up as a drop in the index along the preform axis, as shown by curve 71.

Figure 8:
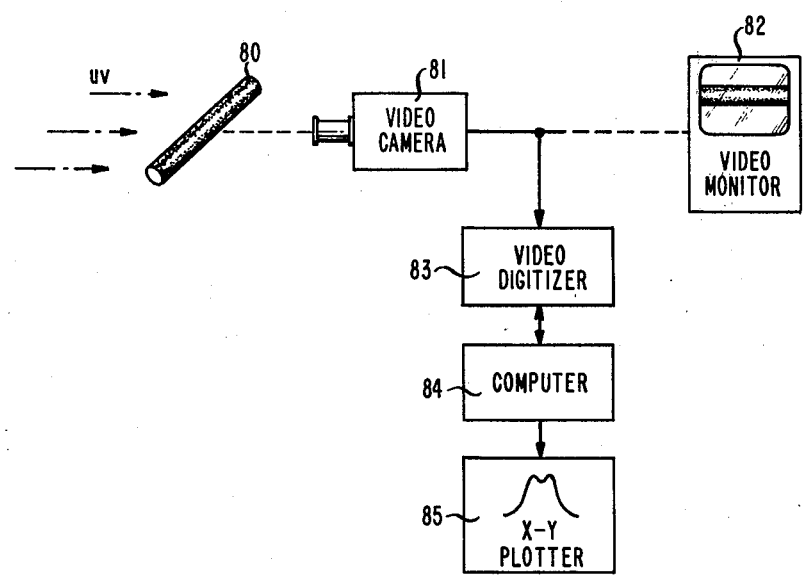
FIG. 8 shows the arrangement of apparatus for obtaining the curves of FIG. 7.

As indicated hereinabove, the entire process can be automated using commercially available equipment, as illustrated in FIG. 8. In the particular arrangement employed to obtain the preform curves shown in FIG. 7, the illuminated fiber/preform 80 is viewed by a video camera 81 (RCA model TC1005). For this purpose, the camera is fitted with a Nikon MACRO lens. When viewing a fiber, the camera is fitted with a microscope lens.

The output from the camera is optionally coupled to a video monitor 82 for viewing, and to a video digitizer 83 (Colorado Video Inc., model 260) which, under the control of a computer 84 (Hewlett-Packard, model 9825A), scans the light intensity at any prescribed location along the fiber/preform. The information thus obtained is then coupled to the computer which solves the integral (2). The solution is transmitted to an x-y plotter 85 (Hewlett-Packard model 9862A) which generates the intensity distribution curve (i.e., curve 70, FIG. 7) and the dopant distribution curve (i.e., 71). If the fiber/preform contains only a single dopant, the dopant distribution curve is also the index profile curve. If more than one dopant is present, the computer will combine the effect of each of the plurality of dopants and generate a net profile curve. The entire process is completed in a matter of minutes.

The methods outlined hereinabove give relative values. If absolute dopant concentrations are desired, the system can be calibrated using a slide having a known dopant concentration distribution. The slide is exposed to ultraviolet light in the same manner as the fiber/preform and a reference light intensity is obtained. Light from the fiber/preform is then compared to the reference level to obtain absolute dopant concentrations.

Having obtained the desired profile information about a preform, the latter can then be suitable marked and a fiber drawn therefrom only over the useful portion of the preform. The marking can be such as to automatically terminate the fiber drawing process by providing means for sensing the preform markings and for causing the fiber drawing equipment to respond to signals generated by such markings. This would avoid drawing fibers from portions of the preform found to be defective or otherwise undesirable for use as a source of high quality optical fiber.

We claim:

1. A method of determining the dopant concentrations in optical fibers and fiber preforms CHARACTERIZED BY THE STEPS OF:

illuminating a length of a fiber/preform with a source of ultraviolet radiation;

determining, along a direction transverse to the longitudinal axis of said fiber/preform, the intensity distribution of radiant energy derived from said fiber/preform; and determining from said intensity distribution, the concentration of dopant as a function of distance from the center of the fiber/preform.

2. The method according to claim 1 CHARACTERIZED IN THAT:

the radiant energy measured is the fluorescent light produced by the dopant whose concentration is to be determined.

3. The method according to claim 1 CHARACTERIZED IN THAT:

the radiant energy measured is the ultraviolet light that has traversed the fiber/preform.

4. The method according to claim 1 CHARACTERIZED IN THAT:

the relationship between the measured light intensity P(y) and the dopant concentration $\rho(r)$ is given by $$\rho(r) = -\frac{2}{\pi K} \int_r^a \frac{dP(y)}{dy} \frac{dy}{\sqrt{y^2 - r^2}}$$

where r assumes all values between zero and a.

5. The method according to claim 1 wherein said fiber/preform contains a plurality of different dopants; CHARACTERIZED IN THAT:

said method is repeated for each of said dopants using a different wavelength of ultraviolet light for each dopant.

* * * * *